United States Patent [19]

Grollier et al.

[11] 4,314,807

[45] Feb. 9, 1982

[54] HAIR DYE COMPOSITION CONTAINING A HAIR DYE FORMULATION PACKAGED IN TWO PARTS

[75] Inventors: Jean-François Grollier, Paris; Christian Monnais, Neuilly-sur-Seine; Lyonnel Peritz, Boulogne-sur-Sein, all of France

[73] Assignee: L'Oreal, Paris, France

[21] Appl. No.: 742,117

[22] Filed: Nov. 15, 1976

[30] Foreign Application Priority Data

Nov. 13, 1975 [LU] Luxembourg ............................ 73793
Nov. 13, 1975 [LU] Luxembourg ............................ 73794
Nov. 13, 1975 [LU] Luxembourg ............................ 73795

[51] Int. Cl.$^3$ .............................................. A61K 7/13
[52] U.S. Cl. ............................................ 8/406; 8/553; 8/554; 8/555
[58] Field of Search ................ 8/10.2, 11, 32; 424/70, 424/DIG. 2, 71; 252/DIG. 2, DIG. 3

[56] References Cited

U.S. PATENT DOCUMENTS

| | | | |
|---|---|---|---|
| 3,712,158 | 1/1973 | Kalopissis et al. | 8/10.2 |
| 3,849,548 | 11/1974 | Grand | 424/70 |
| 3,876,760 | 4/1975 | Nersesian et al. | 424/70 |
| 3,912,808 | 10/1975 | Sokol | 424/70 X |
| 3,917,817 | 11/1975 | Vanlerberghe et al. | 424/70 |
| 3,948,596 | 4/1976 | Kalopissis et al. | 8/10.2 |
| 3,980,769 | 9/1976 | Ghilardi et al. | 424/70 |
| 3,986,825 | 10/1976 | Sokol | 8/10.2 X |
| 4,009,256 | 2/1977 | Nowak et al. | 424/70 |

*Primary Examiner*—Natalie Trousof
*Assistant Examiner*—Vera C. Clarke
*Attorney, Agent, or Firm*—Cushman, Darby & Cushman

[57] ABSTRACT

A process for dyeing hair comprises in sequence applying to the hair an oxidation hair dye composition comprising a mixture of an oxidation dye, a cationic polymer and an oxidizing agent in an oxidation dye carrier, permitting said oxidation hair dye composition to remain in contact therewith for a time ranging from about 15–40 minutes, rinsing the hair with water, then applying to the rinsed hair a shampoo composition containing an anionic detergent and thereafter rinsing said hair with water.

1 Claim, No Drawings

HAIR DYE COMPOSITION CONTAINING A HAIR DYE FORMULATION PACKAGED IN TWO PARTS

The present invention relates to a new cosmetic composition as well as to a process for using this new composition. More precisely, the present invention relates to a new composition for dyeing living human hair as well as to a process for dyeing hair with said composition.

It is known that various hair dye compositions up to now often exhibit the disadvantage of rendering the hair dull and hard. To overcome this disadvantage, that is, to restore to the hair the favorable characteristics it possessed before the dyeing operation, it has been proposed to treat the hair with cationic products, these products being applied after the dyeing operation and before a final setting of the hair. However, it has been noted that this supplemental operation also provides certain disadvantages and does not always impart with certainty good cosmetic properties to the hair.

It has now been found that it is possible to dye the hair without deleteriously interfering with the brightness or luster or the softness to the touch of the hair by employing the composition of the present invention.

The invention thus relates to a new composition for dyeing hair which comprises a combination of two specific formulations which are applied sequentially to the hair.

These specific formulations are a hair dye formulation comprising a conventional oxidation hair dyeing composition containing a hair dye or dye precursors in admixture with at least one cationic polymer, and a shampoo formulation to be applied immediately following the use of the said hair dye formulation and containing at least one anionic detergent. Preferably, the shampoo formulation also contains at least one cationic polymer.

It has now been found, through extensive research, that the application of the said hair dye formulation followed by the application of the said shampoo formulation provides particularly satisfying results, especially with regard to untangling of wet hair, while at the same time imparting to dry hair such interesting cosmetic properties as luster, brightness, softness to the touch, excellent untangling and remarkable ease of styling characteristics.

The hair dye formulation employed in the composition of the present invention is an oxidation hair dye composition comprising in addition to a cationic polymer, an oxidation dye component and a conventional carrier.

It is known that oxidation hair dye compositions employ dyes termed "oxidation dyes" which are aromatic compounds of the diamine, amino phenol or phenol type. These aromatic compounds are dye precursors which are transformed into dye compounds by condensation in the presence of a large excess of an oxidizing agent, generally $H_2O_2$. Among the oxidation dyes, there are on the one hand "bases" which are ortho- or para diamines or mono- or di-ortho or para amino phenols and, on the other hand, "modifiers" which are meta-diamines, meta-amino phenols or polyphenols.

The "bases" principally employed are paraphenylenediamine, para-toluylenediamine, chloroparaphenylenediamine, para-aminodiphenylamine, orthophenylenediamine, ortho-toluylenediamine, 2,5-diaminoanisole, ortho-amino phenol and para-amino phenol.

The "modifiers" principally employed are: meta-phenylenediamine, meta-toluylenediamine, 2,4-diaminoanisole, meta-amino phenol, pyrocatechol, resorcinol, hydroquinone, α-naphthol, 1,5-dihydroxy naphthalane and 2,6-diamino pyridine. The "bases" are also termed "base oxidation dyes" while the "modifiers" are also called "couplers".

The oxidation dyeing composition contains principally, besides the cationic polymer, a mixture of bases and modifiers, with a conventional carrier. Preferably, the carrier is one which provides the said composition in the form of a cream or gellable liquid. Representative carriers include, principally, fatty acids, fatty amides, alkyl sulfates, polyoxyethylenated alkyl sulfates and water, in varying amounts.

In the oxidation hair dyeing composition used in the present invention, the various components thereof can be provided in the following amounts, by weight:

| | |
|---|---|
| Basic oxidation dyes | 0.003–7% |
| Couplers | 0.001–4% |
| Fatty Acids | 0–25% |
| Fatty Amides | 0–12% |
| Alkalizing Agent | 0.5–20% |
| Alkyl sulfates, oxyethylenated or not | 0–10% |
| Fatty Alcohols, oxyethylenated or not | 0–20% |

In addition to the oxidation hair dyes, the hair dye formulation can contain direct dyes such as azo, anthraquinone, nitrobenzene, indamine, indoaniline and indophenol dyes or other oxidation dyes such as the leuco-derivatives of these compounds.

Representative fatty acids usefully employed in the hair dye formulation include: lauric acid, oleic acid, isostearic acid, myristic acid, palmitic acid, ricinoleic acid and stearic acid.

Representative fatty amides include mono- or diethanolamides of the fatty acids of copra and the mono- or diethanolamides of oleic acid.

Representative alkyl sulfates, oxyethylenated or not, usefully employed in the hair dye formulation, include sodium lauryl sulfate, sodium cetylstearyl sulfate, triethanolamine cetylstearyl sulfate, triethanolamine lauryl myristyl sulfate, monoethanolamine lauryl sulfate, sodium lauryl ethersulfate oxyethylenated with, for example, 2.2 moles of ethylene oxide and monoethanolamine laurylether sulfate oxyethylenated with, for example, 2.2 moles of ethylene oxide.

The pH of the hair dye formulation generally ranges between 9 and 11 and it can be regulated by the addition of an appropriate alkalizing agent to the hair dye carrier, for example by the addition of ammonia, monoethanolamine, diethanolamine or triethanolamine.

When the hair dye formulation is provided in the form of a gel or gellable liquid, other components can be present such as for example lower alcohols and preferably ethyl alcohol, isopropyl alcohol or propyl alcohol; glycols and principally propylene glycol, butyl glycol and Cellosolve; as well as non-ionic compounds oxyethylenated or polyglycerolated, and principally nonylphenol polyoxyethylenated with, for example, 4 moles or 9 moles of ethylene oxide, oleyl alcohol polyglycerolated with for example 2 or 4 moles of glycerol, and $C_9$–$C_{15}$ synthetic fatty alcohols polyoxyethylenated with, for example, 3 or 10 moles of ethylene oxide. These non-ionics are present in an amount of 0–50 weight percent of said formulation.

When the hair dye formulation of the present invention is provided in the form of a cream, it can also contain, principally, natural or synthetic $C_9$–$C_{20}$ fatty alcohols, saturated or unsaturated, such as cetyl stearyl alcohol, oleyl alcohol, lauryl alcohol and isostearyl alcohol.

Representative cationic polymers which can be employed in the present invention in the hair dye formulation component, include:

1. The quaternary derivatives of cellulose ethers of the formula

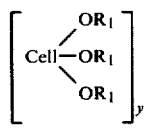  I wherein Cell represents the residue of an anhydroglucose unit, y represents a whole number ranging between about 50 and about 20,000, and preferably between about 200 and about 5,000, and each $R_1$ independently represents a group of the formula:

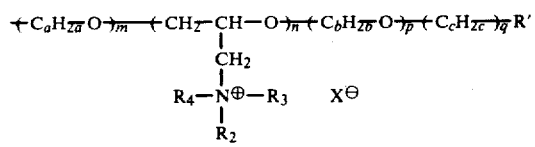

wherein a and b are whole numbers equal to 2 or 3; c is a whole number equal to 1, 2 or 3; m and p are whole numbers ranging from 0 to 10; n is a whole number ranging from 0 to 3; q is a whole number ranging from 0 to 1; $R_2$, $R_3$ and $R_4$ represent alkyl, aryl, aralkyl, alkylaryl, alkoxyalkyl or alkoxyaryl group, said group containing up to 10 carbon atoms, and such that the sum of the number of carbon atoms of $R_2$, $R_3$ and $R_4$ ranges from 3–12. When the said group is alkoxy alkyl, there are at least two carbon atoms between the oxygen atom and the nitrogen atom. R' represents hydrogen, or when q=O, a carboxyl, optionally salified; and $X^\ominus$ represents a mineral or organic anion.

Representative $X^\oplus$ anions include chloride, bromide, iodide, sulfate, bisulfate ($HSO_4^\oplus$), $CH_3SO_3^\oplus$, sulfonate, phosphate, acetate and the like.

The average value of n is between about 0.01 and 1 per anhydroglucose unit, preferably between about 0.1 and 0.5.

The average value of (m+n+p+q) is between about 0.01 and 4 per anhydroglucose unit and preferably between 0.1 and 2.5.

Such quaternary derivatives of cellulose ether are particularly described in French Pat. No. 1,492,597. The quaternary derivatives of cellulose ether can be prepared according to procedures described in this patent, by etherification and quaternization, these two operations being able to be made in either order or simultaneously.

The etherification stage effects the fixation on the cellulose chain of a short chain alkyl or hydroxyalkyl group having, for example, up to 4 carbon atoms, preferably an alkyl group having from 1 to 3 carbon atoms or a hydroxy alkyl group having from 2 to 4 carbon atoms.

To carry out the etherification there is employed principally an alkylation agent such as dimethyl sulfate, diethyl sulfate, methyl chloride, methyl bromide, ethyl chloride, ethyl bromide or n-propyl chloride or a carboxy-alkylation agent or a hydroxy alkylation agent such as ethylene oxide or propylene oxide.

For the quaternization reaction, there is employed a quaternary halogenhydrin having the formula

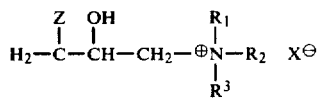

or a quaternary epoxide of the formula:

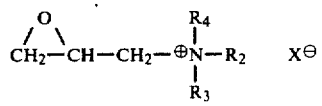

wherein $R_2$, $R_3$ and $R_4$ have the meanings given above, Z is chlorine, bromine or iodine and $X^\ominus$ is an anion, preferably an anion of a strong mineral acid.

The radicals $R_1$ fixed on the anhydroglucose chain can be, as an example, the following: H; —$CH_3$; —$C_2H_5$; —$CH_2$—$CH_2$—OH; —($CH_2$—$CH_2$—O)$_s$—$CH_2OH$, wherein s is a whole number, for example, 1 or 2;

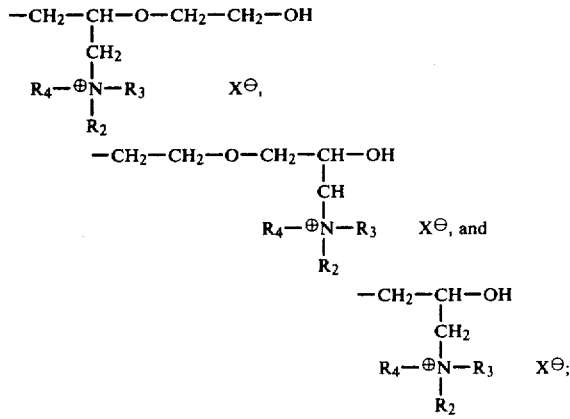

wherein $R_2$, $R_3$ and $R_4$ have the meanings given above, and represent, for example, methyl or ethyl radicals, and $X^\ominus$ represents, for instance, chlorine.

Representative quaternary derivatives of cellulose ether include the polymer formed by the reaction of hydroxyethyl cellulose (having a degree of substitution in hydroxyethyl groups of 1.3) with the reaction product of 0.7 moles of epichlorohydrin and 0.7 moles of trimethylamine per unit of substituted anhydroglucose, this polymer having an average molecular weight of 200,000 to 230,000.

The degree of substitution by groups having a quaternary nitrogen must be such that the molecular weight of the substituted hydroxyethyl cellulose polymer ranges between about 2,000 and 3,000,000.

When the quaternized polymer of cellulose ether is prepared from cellulose ether, the latter is preferably selected from non-ionic water soluble cellulose ethers, substituted by a short chain alkyl or hydroxy alkyl group. These derivatives are principally the methyl-, ethyl- or hydroxyethyl cellulose.

Representative quaternized derivatives of cellulose ether usefully employed in the present invention include such commercial products as JR-125, JR-400 and JR30M, sold by Union Carbide;

2. Cyclopolymers containing units of the formula

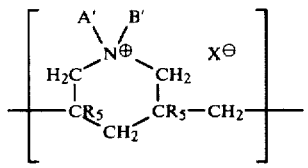
II where $R_5$ is hydrogen or methyl and A' and B' each independently represent alkyl having 1-22 carbon atoms, principally methyl or ethyl, lower hydroxy alkyl or lower alkyl having terminal amido groups, or A' and B' taken together with the nitrogen atom to which they are attached form a piperidinyl or morpholinyl group, and X has the meaning given above, or cyclopolymers consisting of homopolymers or copolymers containing units of the formula

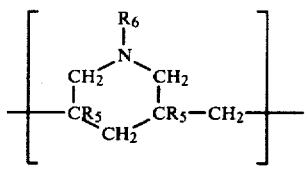
III wherein $R_5$ is hydrogen or methyl, $R_6$ is hydrogen or alkyl having from 1-22 carbon atoms or hydroxy lower alkyl having from 1-5 carbon atoms or a lower alkyl containing a terminal amido group such as a beta-propionamido group, or copolymers obtained from acrylamide or diacetone acrylamide and monomers furnishing in the copolymer units having the formula

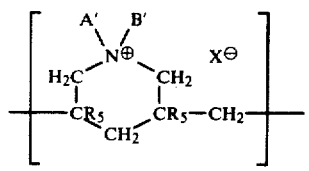
IV wherein $R_5$ has the meaning given above and A' and B' each independently represent alkyl having 1-22 carbon atoms, preferably 1-5 carbon atoms, hydroxy lower alkyl, or lower alkyl containing a terminal amido group, such as beta-propionamido, or, A' and B' together with the nitrogen atom to which they are attached, form a piperidinyl or morpholinyl group.

The copolymers mentioned above contain units of the formula:

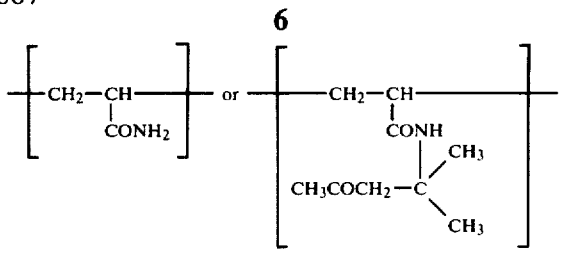

The cyclopolymers, and corresponding copolymers, are described particularly in French Pat. No. 71.06387 and its Certificate of Addition, No. 73.23970.

Every non-toxic, cosmetically acceptable anion, organic as well as mineral, represented by $X^{\ominus}$, can be present in the polymer and associated with the cationic quaternary ammonium. Representative anions include acetate, borate, bromide, chloride, citrate, tartrate, bisulfate, bisulfite, sulfate, phosphate or succinate. The homopolymers and copolymers of formula III can be prepared as described in U.S. Pat. No. 2,926,161 by polymerizing an appropriate diallylamine or amine salts. The copolymers of formula IV can be prepared by polymerizing a diallyldialkyl ammonium chloride or bromide or other suitable monomer salts of diallyl ammonium with a free radical polymerization catalyst such as a peroxide, then optionally by using an ion exchange column, such as described in U.S. Pat. Nos. 3,288,770 and 3,412,019.

The polymers of formulas II to IV have a molecular weight between 20,000 and 3,000,000;

3. Quaternized polymers comprising recurring units of the formula

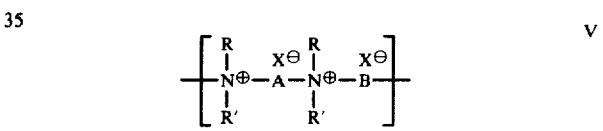
V wherein:

$X^{\ominus}$ represents an anion derived from a mineral or organic acid; R is lower alkyl or $—CH_2—CH_2OH$; R' is aliphatic, alicyclic or arylaliphatic, such that R' contains a maximum of 20 carbon atoms; or R and R' attached to the same nitrogen atom form with it a ring capable of containing a second heteroatom other than nitrogen; A represents a divalent group of the formula

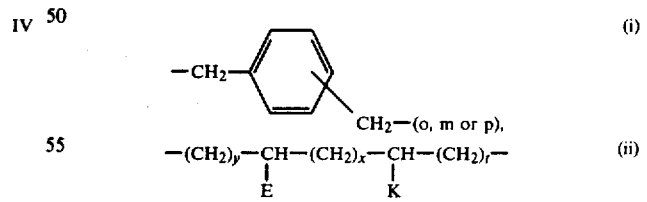

wherein x, y and t are whole numbers ranging from 0 to 11 and such that the sum (x+y+t) is greater than or equal to 0 and lower than 18, and E and K represent hydrogen or an aliphatic radical having less than 18 carbon atoms, (iii) $—(CH_2)_a—S—(CH_2)_a—$
(iv) $—(CH_2)_a—O—(CH_2)_a—$
(v) $—(CH_2)_a—S—S—(CH_2)_a—$
(vi) $—(CH_2)_a—SO—(CH_2)_a—$
(vii) $—(CH_2)_a—SO_2—(CH_2)_a—$ or

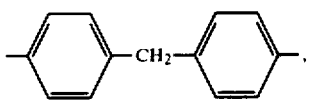

(viii)

wherein a is a whole number equal to 2 or 3; B represents a divalent group of the formula:

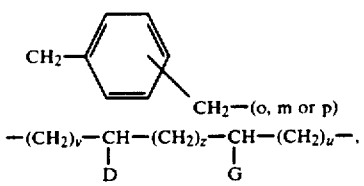

(i)

$$-(CH_2)_v-CH-(CH_2)_z-CH-(CH_2)_u-.\qquad\text{(ii)}$$
$$\phantom{-(CH_2)_v-C}|\phantom{H-(CH_2)_z-C}|$$
$$\phantom{-(CH_2)_v-C}D\phantom{H-(CH_2)_z-C}G$$

wherein D and G represent hydrogen or an aliphatic radical having less than 18 carbon atoms, and v, z and u are whole numbers ranging from 0 to 11, two of them being able simultaneously to be equal to 0, such that the sum (v+z+u) is greater than or equal to 1 and lower than 18, and such that the sum (v+z+u) is greater than 1 when the sum (x+y+t) is equal to 0,

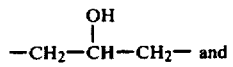

(iii)

(iv) —(CH$_2$)$_a$—O—(CH$_2$)$_a$—, wherein a has the meaning given above.

The terminal groups of the polymers of formula V can vary with the amount of the initial reactants employed and can be of the type

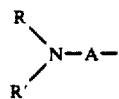

or of the type X— B—, wherein R, R', A, X and B have the meanings given above.

In formula V, $X^\ominus$ represents principally a halide anion such as bromide, iodide or chloride, or an anion derived from other mineral acids such as phosphoric acid or sulfuric acid, and the like, or even an anion derived from an organic sulfonic or carboxylic acid, principally an alkanoic acid having from 2-12 carbon atoms, such as acetic acid, a phenyl alkanoic acid such as phenyl acetic acid, benzoic acid, lactic acid, citric acid, or paratoluene sulfonic acid. The substituent R represents preferably alkyl having from 1-6 carbon atoms. When R' represents an aliphatic radical, this radical is generally alkyl or cycloalkyl wherein the alkyl has less than 20 carbon atoms and preferably not more than 16 carbon atoms. When R' represents an alicyclic radical, this radical is generally cycloalkyl having 5 or 6 chains. When R' represents an aryl aliphatic radical, this radical is generally aralkyl such as phenyl alkyl wherein the alkyl moiety has, preferably, from 1-3 carbon atoms. When R and R' attached to the same nitrogen atom constitute with it a ring, R and R' can represent together principally polymethylene having from 2-6 carbon atoms, and the ring can carry a second heteroatom, for example, oxygen or sulfur. When the substituent E, K, D or G is an aliphatic radical, this radical is generally alkyl having from 1-17 carbon atoms, and preferably from 1-12 carbon atoms;

v, z and u represent preferably numbers ranging from 1 to 5 and two of them can be equal to 0; x, y and t are preferably numbers ranging from 0 to 5. When A or B represents a xylylidenyl radical, it can be o-, m- or p-xylylidenyl. Further, A, B, R and R' can have several different values in the same polymer V.

The polymers of formula V usefully employed in the present invention can have a molecular weight ranging generally between 5,000 and 50,000. The polymers of formula V are described principally in French Pat. No. 75.15162 filed May 15, 1975;

4. Quaternized polymers having recurring units of the formula

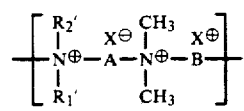

VI wherein $X^\ominus$ represents an anion derived from an organic or mineral acid;

R'$_2$ is an aliphatic radical having a maximum of 20 carbon atoms;

R'$_1$ is an aliphatic, alicyclic or aryl aliphatic radical having a maximum of 20 and a minimum of 2 carbon atoms, or R'$_1$ and R'$_2$ together form, with the nitrogen atom to which they are attached, a ring optionally carrying another heteroatom;

A represents a divalent group of the formula

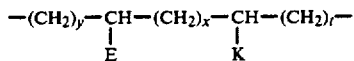

wherein x, y and t are whole numbers ranging from 0 to 11 and such that the sum (x+y+t) is greater than or equal to 0 and lower than 18, and E and K represent hydrogen or an aliphatic radical having less than 18 carbon atoms;

B represents a divalent group of the formula:

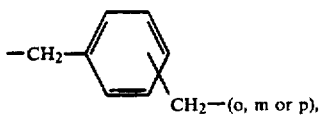

—CH$_2$—CHOH—CH$_2$——(CH$_2$)$_n$—O—(CH$_2$)$_n$— or

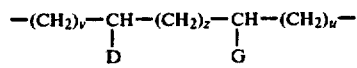

wherein D and G represent hydrogen or an aliphatic radical having less than 18 carbon atoms, and v, z and u are whole numbers ranging from 0 to 11, two of them being able simultaneously to be equal to 0, and such that the sum (v+z+u) is greater than or equal to 1 and lower than 18, such that the sum (v+z+u) is greater than 1 when the sum (x+y+t) is equal to 0, and n is whole number equal to 2 or 3.

The terminal groups of the polymers of formula VI can vary principally with the amount of initial reactants and can be of the type R'$_2$R'$_1$—N—A—, (CH$_3$)$_2$N—A— or X—B—.

In formula VI, X⊖ represents principally a halide anion such as bromide, iodide or chloride, or an anion derived from other mineral acids such as phosphoric acid or sulfuric acid, or even an anion derived from an organic sulfonic or carboxylic acid, principally an alkanoic acid having 2–12 carbon atoms, such as acetic acid, a phenyl alkanoic acid such as phenyl acetic acid, benzoic acid, lactic acid, citric acid, or paratoluene sulfonic acid. When $R'_1$ represents an aliphatic radical, this radical is generally alkyl or cycloalkyl wherein the alkyl has less than 20 carbon atoms and preferably not more than 16 carbon atoms. When $R'_1$ represents an alicyclic radical, this radical is generally cycloalkyl having 5 or 6 chains. When $R'_1$ represents an aryl aliphatic radical, this radical is generally aralkyl such as phenyl alkyl wherein the alkyl moiety contains preferably from 1 to 3 carbon atoms. When the substituent E, K, D or G is an aliphatic radical, this radical is generally alkyl having from 1–17 carbon atoms and preferably from 1–2 carbon atoms; v, z and u represent preferably numbers ranging from 1 to 5, two of them capable of being equal to be 0; x, y and t are preferably numbers ranging from 0 to 5. When B represents a xylylidenyl radical, this radical can be o—, m— or preferably p-xylylidenyl.

The polymers of formula VI can be prepared by one of the following procedures:

(a) a di-tertiary diamine of the formula $R'_2R'_1N-A-N(CH_3)_2$ is polycondensed with a dihalide of the formula $X-B-X$, in which A, B, $R'_1$, $R'_2$ and X have the meanings given above; or (b) a di-tertiary diamine of the formula $R'_1R'_2N-B-N(CH_3)_2$ is polycondensed with a dihalide of the formula $X-A-X$.

In place of the above starting reactants, there can be employed either a mixture of di-tertiary diamines, or a mixture of dihalides, or even a mixture of di-tertiary diamines and a mixture of dihalides, providing that the ratio of total molar quantities of diamines to dihalides is close to 1.

Di-tertiary diamines employed as an initial reactant in the above described process are known or can be prepared by using known methods. For example, di-tertiary diamines of the formula $R'_2R'_1N-(CH_2)_n-N(CH_3)_2$, wherein $n=3$, can be prepared by cyanoethylation of a secondary amine of the formula $R'_2R'_1NH$ in accordance with Whitmore et al, J.A.C.S. 66 p. 725 (1944); reduction of the propionitrile amine; and methylation by the Eschweiler-Clarke method using a formaldehyde-formic acid mixture. (cf. Chem Ber., 38, p. 880 (1905) and J.A.C.S., 55 p. 4571 (1933).

The other di-tertiary diamines can be prepared by methylation, according to the method described above, of diamines of the formula $R'_2R'_1N-A-NH_2$ or $R'_1HN-A-NH_2$, which in turn can be obtained by a method derived from that described by H. E. Franck et al, J.A.C.S., 67 p. 882 (1947) or indeed analogous to the method described in U.S. Pat. No. 3,234,139.

The polymers of formula VI can have a molecular weight generally between 5,000 and 50,000 and are described in Luxembourg patent entitled "New Quaternized Polymers, Their Process of Preparation and Their Use", filed July 4, 1975

5. Graft and crosslinked cationic copolymers, described in French Pat. No. 73.22222, resulting from the copolymerization:

(a) at least one cosmetic monomer,
(b) dimethylaminoethyl methacrylate
(c) polyethylene glycol and
(d) a polyunsaturated crosslinking agent.

This graft and crosslinked copolymer includes those carrying on their principal chain lateral branchings linked between them through the intermediary of transverse links which are established by the action of the crosslinking agent.

The crosslinking agent is selected, for example, from the group consisting of ethylene glycol dimethacrylate, diallyl phthalates, divinylbenzenes, tetraallyloxyethane and polyallylsucroses having from 2–5 allyl groups per mole of sucrose.

The degree of unsaturation of the crosslinking agent can then be at a minimum of 2 and a maximum of 5 in the case of the polyallylsucroses.

The cosmetic monomers can be of various types, for example, the vinyl esters of an acid having 2–18 carbon atoms; allyl or methallyl esters of an acid having from 2–18 carbon atoms; the acrylate or methacrylate of a saturated alcohol having from 1–18 carbon atoms; alkyl vinyl ethers wherein the alkyl moiety has from 2–18 carbon atoms; olefins having from 4–18 carbon atoms; vinyl heterocyclic derivatives; dialkyl maleates or N,N-dialkylaminoalkyl maleates wherein the alkyl moiety has from 1–3 carbon atoms; or the anhydrides of unsaturated acids.

Preferably the cosmetic resin is selected from the group consisting of vinyl acetate, vinyl propionate, methyl methacrylate, stearyl methacrylate, lauryl methacrylate, ethylvinyl ether, cetylvinyl ether, stearylvinyl ether, hexene-1, octadecene, N-vinylpyrrolidone, the mono-maleate of N,N-diethylamino ethyl, maleic anhydride and diethyl maleate.

The prepolymer, on which is effected the grafting, is as indicated above polyethylene glycol having a molecular weight ranging generally between 200 and several million, but preferably between 300 and 30,000.

The preferred graft and crosslinked copolymers are:

(a) from 3 to 95 weight percent of at least one cosmetic monomer as defined above;
(b) from 3–95 weight percent of dimethylaminoethyl methacrylate,
(c) from 2 to 50 weight percent, but preferably from 5 to 30 weight percent, polyethylene glycol; and
(d) from 0.01 to 8 weight percent of a crosslinking agent such as defined above, the percentage of crosslinking agent being expressed relative to the total weights of (a)+(b)+(c).

These graft and crosslinked copolymers can be provided in the form of their quaternary salts. In this case, they result from the copolymerization of previously quaternized dimethylaminoethyl methacrylate or from a later quaternization reaction of the tertiary amine group of dimethylamino ethyl methacrylate. Representative appropriate quaternization agents include dialkyl sulfates such as diethyl sulfate or dimethyl sulfates, benzyl halides, such as benzyl chloride, benzyl bromide or benzyl iodide or alkyl halides, as well as other conventional quaternization agents.

The graft and crosslinked copolymers such as defined above can have a molecular weight ranging between 10,000 and 1,000,000, but preferably between 15,000 and 500,000. These graft and crosslinked cationic copolymers can be prepared in accordance with the process described in French Pat. No. 73.22222;

6. Graft cationic copolymers resulting from the copolymerization of (a) N-vinylpyrrolidone,
(b) dimethylaminoethyl methacrylate and (c) polyethylene glycol.

These graft cationic copolymers are employed in quaternized form resulting from their reaction with a quaternization agent selected from the group consisting of dimethyl sulfate, diethyl sulfate or benzyl chloride, iodide or bromide.

Further, these graft cationic copolymers can be made in accordance with conventional techniques employed for the preparation of copolymers.

The preferred graft cationic copolymers comprise:
(a) from 3-95 weight percent N-vinylpyrrolidone,
(b) from 3-95 weight percent dimethylaminoethyl methacrylate, quaternized or not, and
(c) from 2 to 50 weight percent, but preferably from 5 to 30 weight percent, polyethylene glycol.

The polyethylene glycol used for the production of these graft cationic polymers has generally a molecular weight ranging between 200 and several million, but preferably between 300 and 30,000.

The graft cationic copolymers such as defined above have a molecular weight between 10,000 and 1,000,000 and preferably between 15,000 and 500,000;

7. Cationic copolymers of the formula

wherein $A_2$ represents a radical derived from a heterocycle carrying two secondary amine functions and preferably the radical

and $Z_1$ represents the symbol $B_2$ or $B'_2$; $B_2$ and $B'_2$ each independently represent a bivalent radical which is a branched or straight chain alkylene radical, carrying up to 7 carbon atoms in the principal chain, not substituted or substituted by hydroxyl groups and capable of carrying an atom of oxygen, nitrogen or sulfur, or 1-3 aromatic or heterocyclic rings. The oxygen, nitrogen and sulfur atoms can correspondingly be present in the form of a group such as ether, thioether; sulfoxide; sulfone, sulfonium; amine; alkylamine wherein the alkyl can carry an oxygen heteroatom and one or more hydroxyl and/or carboxyl functions; alkenylamine; benzylamine, amine oxide; quaternary ammonium; amide; imide; alcohol; ester and/or urethane. The quaternary ammonium salts and the oxidation products of these polymers of formula VII can also be employed.

Representative preferred polymers include those wherein $A_2$ has the meaning indicated above and $B_2$ and $B'_2$ each independently represent a branched or straight chain alkylene radical having up to 7 carbon atoms in the principal chain, not substituted or substituted by a hydroxyl group, or an alkylene group or hydroxy alkylene having up to 7 carbon atoms interrupted by one or more groups selected from amine, alkylamine, alkenylamine, benzylamine, amine oxide, quaternary ammonium, carboxamide, ether, piperazinyl and/or the group

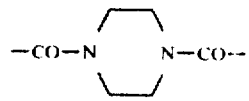

Among these copolymers are, principally, those which are prepared by polyaddition or polycondensation of (a) piperazine or its derivatives such as N,N'-bis-(hydroxyethyl) piperazine with (b) a bifunctional compound such as (1) alkyl or alkylaryl dihalides such as ethylene chloride or bromide, or bis chloromethyl 1,4-benzene; (2) more complex di-halogenated derivatives such as bis(chloroacetyl)ethylene diamine; (3) bis halohydrins such as bis 3-chloro-2-hydroxy propyl ether, or any other bis chlorohydrin obtained in a known manner by condensation of epichlorohydrin (i) on a primary amine optionally hydroxylated, (ii) on a bis secondary diamine such as piperazine, 4,4'-dipiperidyl, bis 4,4'-(n-methylaminophenyl)-methane or N,N'-dimethylethylene diamine or propylene diamine, (iii) on an α-ω-dimercaptoalkane, (iv) on a diol as ethylene glycol or (v) on a bisphenol as hydroquinone or bisphenol A; (4) bis epoxides such as diglycidyl ether or N,N'-bis(2,3-epoxy propyl) piperazine optionally obtained starting with corresponding bis halohydrins; (5) epihalohydrins such as epichlorohydrin or epibromohydrin; (b) bis unsaturated derivatives as divinyl sulfone, bis maleimide derived from ethylene diamine, or even bis acrylamides such as methylene bis acrylamide or piperazine bis acrylamide, derived from bis primary or bis secondary diamines; (7) unsaturated acid as acrylic acid or methacrylic acid or their methyl or ethyl esters; (8) diacids such as succinic, adipic, 2,2,4-trimethyl or 2,4,4-trimethyl adipic acids or terephthalic acid, the chlorides of such acids or the corresponding methyl or ethyl esters; (9) diisocyanates such as toluene diisocyanate or 2,2,4- or 2,4,4-trimethyl hexamethylene diisocyanate. The polyaddition or polycondensation reaction is carried out at ambient pressure and at a temperature between 0° and 100° C., the molar ratio of (a):(b) being from 0.85:1 to 1.15:1.

However, these copolymers can also be prepared in a manner analogous to that starting with N,N'-bis (3-chloro-2-hydroxy propyl) piperazine or starting with N,N'-bis (2,3-epoxy propyl) piperazine and a bifunctional compound such as a bis secondary diamine, a dimercaptan, a diol, a diphenol, a diacid, a primary amine such as an alkylamine, alkenylamine or arylalkylamine, wherein the two hydrogen atoms can be substituted and which behaves as a bifunctional compound.

These copolymers of formula VII can then in a known manner be oxidized with $H_2O_2$ or with peracids, or can even be quaternized with known quaternization reagents, such as a lower alkyl, preferably methyl or ethyl, chloride, bromide, iodide, sulfate, mesylate or tosylate or benzyl chloride or bromide. Further, they can also be condensed with ethylene oxide, propylene oxide, epichlorohydrin or glycidol.

Generally, these copolymers can be prepared in accordance with procedures described in French Pat. No. 72.42279 and its addition No. 74.27030, and can have an average molecular weight ranging between 1,000 and 15,000;

8. Polymers comprising recurring units of the formula

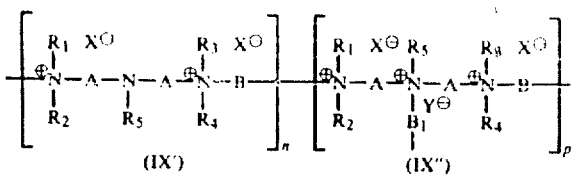

(IX')      (IX")

wherein:

A is polymethylene having 2 or 3 carbon atoms, $B_1$ and B, each independently represent polymethylene having 3-10 carbon atoms; xylylidenyl having the formula $-CH_2-C_6H_4-CH_2-$ ortho, meta or para; $-(CH_2)_x-O-(CH_2)_x-$x being a number equal to 2 or 3; or $-CH_2-CHOH-CH_2-$, $R_1$ and $R_3$ each independently represent an aliphatic radical having 1-12 carbon atoms, $R_2$ and $R_4$ each independently represent an aliphatic radical having 1-20 carbon atoms, $R_5$ is hydrogen, or an aliphatic, alicyclic, aryl or arylaliphatic radical containing a maximum of 20 carbon atoms, $X^\ominus$ represents a halide anion, principally chloride or bromide, $Y^\ominus$ is a halide anion, principally chloride or bromide, and n and p are whole numbers.

The polymers constituted by both units IX' and IX" are called polymers of formula IX.

In formula IX", the $B_1$ group is represented with a free valence, which indicates that the IX" units are bound through a crosslinking bond with similar units of another macromolecular chain.

Thus, polymers of formula IX can have the following structure:

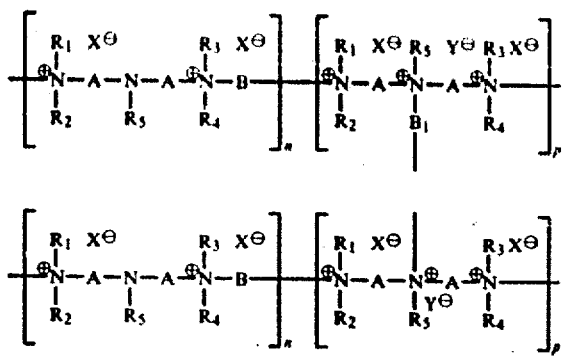

wherein $R_1$ and $R_3$ represent, principally, alkyl having 1-12 carbon atoms;

$R_2$ and $R_4$ represent principally alkyl having 1-20 carbon atoms;

when $R_5$ represents an aliphatic radical, this radical is generally alkyl or cycloalkyl wherein the alkyl has at most 20 carbon atoms, and preferably from 1 to 16 carbon atoms; when $R_5$ represents an alicyclic radical, this radical is generally cycloalkyl having 5 or 6 chains; when $R_5$ represents an arylaliphatic radical, this radical is generally aralkyl radical such as a phenyl alkyl wherein the alkyl moiety has preferably from 1-3 carbon atoms and is, particularly, benzyl.

Preferably $R_1=R_3=CH_3$ with $R_2=R_4$.

The terminal groups of the polymers of formula IX can be $-B_1-Y$ or $-B-X$ wherein $B_1$, B, Y and X have the meanings given above.

The polymers of formula IX wherein $B_1=B$ can be prepared by polycondensing a triamine of the formula:

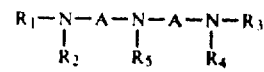

with an excess of a dihalide of the formula:

$$X-B-X$$

wherein $R_1$, $R_2$, $R_3$, $R_4$, $R_5$, A, B and X are defined above.

The dihalide is used in excess, that is, for one mole of triamine employed, the dihalide is employed in an amount greater than one mole.

The polymers of formula IX wherein $B_1$ is different from B can be prepared, as before, by polycondensing a triamine with an essentially equimolar amount of a dihalide. The resulting intermediate polymer of formula IX' is then reacted with a compound of the formula $Y-B_1-Y$, wherein $B_1$ and Y have the meanings given above. The compound $Y-B_1-Y$ can be reacted either by adding the same to the reaction medium, or by first isolating the intermediate polymer IX' and re-dissolving it in an appropriate solvent and then adding thereto the said $Y-B_1-Y$ compound.

In both procedures described above, the reaction can be carried out in a solvent or in a mixture of solvents favoring quaternization reactions. Representative solvents include water, dimethyl formamide, acetonitrile and lower alcohols, principally lower alkanols such as methanol and the like.

The temperature of the reaction can range between 10° and 150° C., and preferably between 20° and 100° C.

The time of the reaction depends on the nature of the solvent selected, the initial reactants chosen and the degree of polymerization desired.

The resulting polycondensate is isolated if desired at the termination of the reaction by, for instance, either filtration, or by concentrating the reaction mixture.

The average length of the polymer chain can be regulated by adding at the beginning of the reaction or during the course thereof, a small amount, 1 to 15 mole percent relative to the triamine, of a mono-functional reactant such as a tertiary amine.

In this case, a portion at least of the terminal groups of the resulting polymer IX comprises the tertiary amine group utilized.

In both processes for preparing polymers of formula IX, the final product is isolated at the termination of the reaction either by filtration, or by concentration of the reaction mixture. Optionally the isolated polymer can be subjected to a crystallization technique by the addition of an appropriate anhydrous organic liquid.

The polymers of formula IX wherein $B_1$ is different from B are prepared by using reactant $Y-B_1-Y$ in any amount up to a maximum of 3 moles per mole of starting triamine. Preferably, from 0.1 to 3 moles of $Y-B_1-Y$ per mole of triamine are employed. The polymers of formula IX are then isolated under conditions favoring the removal of the excess $Y-B_1-Y$ reactant.

In accordance with these procedures, an extensive variety of polymers IX having various degrees of crosslinking and carrying a statistical distribution of units of formula IX' and IX" can be prepared.

The initial triamine reactant employed can be obtained in accordance with methods described in the literature.

The polymers of formula IX are described in Luxembourg patent entitled "New Cosmetic Agents Based on Crosslinked Quaternized Polymers" filed Nov. 13, 1975 under the number 73 794; or in copending U.S. application Ser. No. 742,116, filed Nov. 15, 1976, now abandoned;

9. Polymers comprising recurring units of the formula

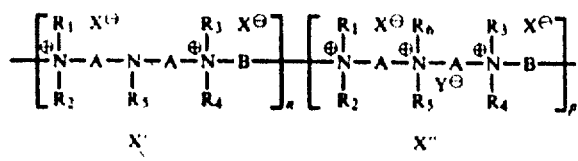

wherein

A is polymethylene having 2–10 carbon atoms;

B is selected from polymethylene having 3–10 carbon atoms, a xylylidenyl group having the formula —CH$_2$—C$_6$H$_4$—CH$_2$13 ortho, meta or para, —(CH$_2$)$_x$—O—(CH$_2$)$_x$— x being 2 or 3, or —CH$_2$—CHOH—CH$_2$—;

R$_1$ and R$_3$ each independently represent an aliphatic radical having 1–12 carbon atoms;

R$_2$ and R$_4$ each independently represent an aliphatic radical having 1–20 carbon atoms;

R$_5$ is hydrogen or an aliphatic, alicyclic, aryl or arylaliphatic radical containing a maximum of 20 carbon atoms;

R$_6$ is an aliphatic or arylaliphatic radical containing a maximum of 20 carbon atoms;

X$^\ominus$ represents a halide anion, principally chloride or bromide;

Y$^\ominus$ is a halide anion, principally chloride or bromide, or a bisulfate anion, SO$_4$H$^\ominus$ or a methosulfate anion, CH$_3$SO$_4^\ominus$;

n and p are whole numbers with p being able to be equal to 0, such that the ratio p/n+p ranges from 0 to 0.95.

In that which follows, the polymers consisting only of units X' are called polymers of formula X'. Polymers consisting of both units X' and X" are called polymers of formula X". To designate indifferently the polymers of X' and X" the term employed is polymers of formula X.

In the polymers of formula X:

R$_1$ and R$_3$ represent, principally, alkyl having 1–12 carbon atoms;

R$_2$ and R$_4$ represent, principally, alkyl having 1–20 carbon atoms;

when R$_5$ or R$_6$ represent an aliphatic radical, this radical is generally alkyl or cycloalkyl wherein the alkyl has at most 20 carbon atoms, and preferably from 1–16 carbon atoms; when R$_5$ represents an alicyclic radical, this radical is generally cycloalkyl having 5 or 6 chains; when R$_5$ or R$_6$ represents an arylaliphatic radical, this radical is generally aralkyl such as phenylalkyl of which the alkyl moiety has preferably from 1–3 carbon atoms and is, particularly, benzyl.

Preferably R$_1$=R$_3$=CH$_3$, with R$_2$=R$_4$.

The terminal groups of the polymers of formula X' can be —A—NR$_1$R$_2$, —ANR$_3$R$_4$ or —B—X.

The terminal group of the polymers of formula X" can be —B—X or —NR$_1$R$_2$R$_6 \oplus$ Y$^\ominus$ or —NR$_1$R$_4$R$_6 \oplus$ Y$^\ominus$.

The polymers of formula X' can be prepared by polycondensing a triamine of the formula

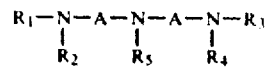

with an essentially equimolar amount of a dihalide of the formula

wherein R$_1$, R$_2$, R$_3$, R$_4$, R$_5$, A, B and X have the meanings given above.

The polymers of formula X" can be prepared by polycondensing the triamine and the dihalide and then reacting the resulting intermediate polymer of formula X' with a compound of the formula R$_6$—Y, R$_6$ and Y having the meanings given above.

The compound R$_6$—Y can be reacted either by adding the same to the reaction medium or by first isolating the intermediate polymer X' and re-dissolving it in an appropriate solvent and then adding thereto the said R$_6$—Y compound.

In both processes described above, the polycondensation reaction can be carried out in a solvent or in a mixture of solvents favoring quaternization reactions. Representative solvents include water, dimethylformamide, acetonitrile and lower alcohols, principally lower alkanols as methanol and the like.

The temperature of the reaction can vary between 10° and 150° C., and preferably between 20° and 100° C.

The time of the reaction depends on the nature of the solvent selected, the starting reactants chosen and the degree of polymerization desired.

The resulting polycondensate is isolated, if desired, at the termination of the reaction, by, for instance, either filtration or by concentrating the reaction mixture.

The average length of the polymer chain can be regulated by adding at the beginning of the reaction or during the course thereof a small amount of a monofunctional reactant such as a tertiary amine.

In this case, a portion at least of the terminal groups of the resulting polymer X comprises the tertiary amine group utilized.

In both procedures for preparing the polymers of formula X, the final product is isolated at the termination of the reaction either by filtration, or by concentration of the reaction mixture. Optionally, the isolated polymer can be subjected to a crystallization technique by the addition of an appropriate anhydrous organic liquid.

The polymers of formula X" are prepared by using reactant R$_6$—Y in any amount up to a maximum of 3 moles per mole of starting triamine. Preferably, from 0.1 to 3 moles of R$_6$—Y per mole of triamine are employed. The polymers of formula X" are then isolated under conditions favoring the removal of excess R$_6$Y reactant.

In accordance with the procedures outlined above, an extensive variety of polymers X" can be obtained since they include those having very few units of formula X" (p/n+p close to zero) up to those which include very few units of formula X' (p/n+p being then equal to or slightly less than 0.95).

The polymers X" include then a statistical distribution of units of formulas X' and X".

The initial triamine reactants used can be obtained in accordance with methods described in the literature.

Generally, the polymers of formula X used in accordance with the present invention have a molecular weight ranging from 5,000 to 100,000.

The polymers of formula X are described in Luxembourg Pat. No. 73 795, entitled "New Cosmetic Agents Based on Quaternized Polyamine Polymers" filed Nov. 13, 1975 or U.S. application Ser. No. 742,118, filed Nov. 15, 1976, now abandoned U.S. Pat. No. 4,150,115.

The shampoo formulation employed in the present invention comprises an anionic detergent, optionally in admixture with a non-ionic detergent.

Representative anionic detergents include:

(i) alkaline salts, magnesium salts, ammonium salts, amine salts or amino alcohol salts (principally ethanolamine or isopropylamine) of fatty acids such as oleic acid, ricinoleic acid, fatty acids of copra oil, or hydrogenated copra oil; alkyl sulfates or alkylether sulfates wherein the alkyl moiety is a linear $C_{12}$ to $C_{18}$ chain; sulfated and ethoxylated $C_{12}$ to $C_{18}$ linear alkylamides, $C_{12}$ to $C_{18}$ linear α-olefin sulfonates; carboxylic acids of polyglycolic ethers having the formula AlK—(OCH$_2$—CH$_2$)$_s$—OCH$_2$—CO$_2$H, AlK is a $C_{12}$ to $C_{18}$ linear chain and s is a whole number;

(ii) the condensation products of fatty acids with: sarcosine and its derivatives, isethionates, polypeptides, alkylsulfosuccinates or their derivatives, taurine, methyl taurine and the like;

(iii) sulfosuccinates of $C_{12}$–$C_{18}$ ethoxylated alcohols, or their corresponding $C_{12}$–$C_{18}$ amide derivatives; and (iv) alkylbenzenesulfonates, alkylarylpolyether sulfates, monoglyceride sulfates and the like.

The non-ionic detergents which can be used in admixture with the anionic detergents are principally:

(a) alcohols, diols, alkylphenols, thiols or amides having $C_6$–$C_{18}$ linear chains which can be oxyethylenated, oxypropylenated, glycerolated or glycidoled;

(b) the polycondensates of ethylene oxide and propylene oxide; and (c) compounds of the formula

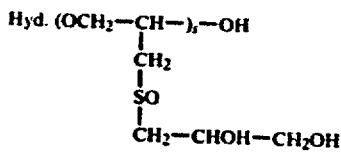

wherein s is a whole number and Hyd represents a hydro carbon radical.

The specific shampoo formulation used according to the present invention contains from 4 to 30 weight percent, preferably, from 5 to 20 weight percent of the anionic detergent.

The non-ionic detergents, when they are present, are used in an amount ranging from 1 to 20 and preferably from 2 to 10 weight percent.

Among the cationic polymers usefully employed in the shampoo formulation are the following:

(A) copolymers of the formula

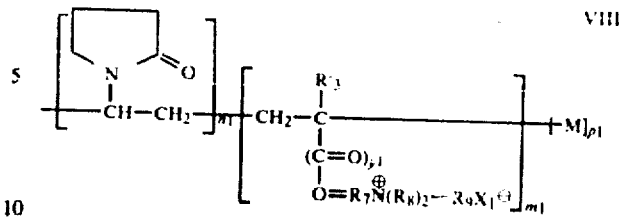 VIII wherein, on the basis of 100 moles of monomer units (i.e. $m_1 + n_1 + p_1 = 100$), $n_1$ is a whole number ranging from 20 to 99, $m_1$ is a whole number ranging from 1 to 80 and $p_1$ is a whole number ranging from 0 to 50; $y_1$ is 0 or 1; $R_7$ represents

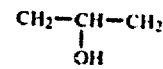

or $C_{x_1}H_{2x_1}$ wherein $x_1$ is a whole number ranging from 2–18; $R_8$ is methyl, ethyl or tert. butyl; $R_9$ is methyl, ethyl or benzyl; $R'_3$ is hydrogen or methyl; $X_1^{\ominus}$ represents a chloride, bromide, iodide, sulfate, bisulfate or $CH_3SO_3^{\ominus}$ anion; and M represents a copolymerizable vinyl monomer unit.

The copolymerizable vinyl monomers optionally present and represented by M in the preceding formula are known vinyl monomers copolymerizable with N-vinylpyrrolidone. These vinyl monomers are principally alkyl vinyl ethers wherein the alkyl moiety has, preferably, 1–8 carbon atoms, for example, methyl vinyl ether, ethyl vinyl ether and octyl vinyl ether; alkyl esters of acrylic or methacrylic acid, principally those wherein alkyl moiety has from 1–4 carbon atoms, for example methyl acrylate or methyl methacrylate; aromatic vinyl monomers such as styrene; α-methyl styrene; vinyl esters such as vinyl acetate; vinylidene chloride; acrylonitrile; methacrylonitrile; acrylamide and methacrylamide, vinyl chloride; and alkyl crotonates wherein the alkyl moiety has, preferably, from 1–8 carbon atoms.

These copolymers can be prepared by copolymerizing N-vinylpyrrolidone with a di-lower alkyl-amino alkyl acrylate or methacrylate, or with a di-lower alkyl aminohydroxy alkyl acrylate or methacrylate, and optionally with another vinyl monomer copolymerizable with vinylpyrrolidone. On a 100% molar basis, vinylpyrrolidone units can represent 20–99%; units derived from the acrylate or methacrylate can represent between 1–80%; and units derived from the other copolymerizable vinyl monomer can represent between 0 and 50%.

Representative acrylates or methacrylates usefully employed in the production of such copolymers include:

dimethylaminomethyl acrylate,
dimethylaminomethyl methacrylate,
diethylaminomethyl acrylate,
diethylaminomethyl methacrylate,
dimethylaminoethyl acrylate,
dimethylaminoethyl methacrylate,
dimethylamino-2-hydroxypropyl acrylate,
dimethylamino-2-hydroxypropyl methacrylate,
diethylamino-2-hydroxyethyl acrylate,
diethylamino-2-hydroxyethyl methacrylate,
dimethylaminobutyl acrylate, dimethylaminobutyl methacrylate,
dimethylaminoamyl methacrylate,
diethylaminoamyl methacrylate,
dimethylaminohexyl acrylate,
diethylaminohexyl methacrylate,
dimethylaminooctyl acrylate,
dimethylaminooctyl methacrylate, and
diethylaminooctyl acrylate.

The molecular weight of these polymers generally ranges between 15,000 and 1,000,000 and more particularly between 50,000 and 500,000.

Representative commercial copolymers of this type include those sold under the trade names Gafquat 734 having a molecular weight of about 10,000 and Gafquat 755 having a molecular weight greater than 1,000,000.

Such polymers are described in French Pat. No. 71.03017;

(B) the quaternary derivative of cellulose ther of formula I described above;

(C) the cyclopolymers of formulas II, III or IV described above;

(D) the quaternized polymers of formulas V or VI described above;

(E) the graft and crosslinked cationic copolymers described above;

(F) the graft cationic copolymers described above;

(G) the cationic copolymers of formula VII described above; and (H) the polymers of formulas IX and X described above.

In the specific hair dye formulation used in accordance with the present invention, the amount of cationic polymer ranges between 0.5 and 10, and preferably between 0.5 and 6, weight percent, relative to the total weight of the hair dye formulation. According to a particular embodiment of this present invention, the specific hair dye formulation is prepared at the moment of use, i.e. the cationic copolymer is added either alone, or in solution in a solvent, for example in an alcohol, in water or in a mixture of water and alcohol, to the dye formulation. Thus, the specific hair dye formulation can be provided in the form of a two-part package, the first part containing the dye carrier and the hair dye precursors or hair dye, and the second part comprising the cationic polymers either alone, or in solution in a solvent.

Preferably the cationic polymer is in an aqueous solution containing, or not, a solvent such as ethyl alcohol, isopropyl alcohol, butyl Cellosolve, ethyl Cellosolve, methyl Cellosolve or propylene glycol. These solutions of the cationic polymer can also contain cosmetic adjuvants such as thickening agents, protein hydroylzates or certain dyes. The pH of these solutions is generally close to neutral.

According to another embodiment of the hair dye formulation of the present invention, the cationic polymer can be incorporated with the dye carrier at the time of its production.

In the specific shampoo formulation, the concentration of the cationic polymer can range between 0.1 and 3, and preferably between 0.3 and 2 percent by weight relative to the total weight of the shampoo formulation. The pH of these shampoo formulations can range between 4 and 9 and preferably between 6 and 8. These shampoo formulations can also contain conventional adjuvants such as dyes, perfumes, sequestering agents, thickening agents and the like.

The present invention also relates to a process for dyeing hair using the composition described above. This process comprises applying to the hair the oxidation dyeing formulation which comprises a mixture of at least one hair dye or dye precursor, an oxidizing agent conventionally employed with said oxidation dyeing formulations and a cationic polymer in an amount sufficient to obtain the desired color, permitting said formulation to remain in contact with the hair for a time ranging between about 15 and 40 minutes, rinsing the hair with water; applying to the rinsed hair a shampoo formulation comprising an anionic detergent; and rinsing the hair with water.

However, before applying the oxidation dyeing formulation to the hair, it is convenient to mix an oxidation dyeing composition with an oxidizing agent conventionally employed with these compositions. These oxidizing agents can be $H_2O_2$ solutions (20 or 30 volumes), urea peroxide, solutions and sodium perborate solutions. A large excess of oxidizing agent is employed in accordance with known techniques for employing oxidation dyes.

The quantity of $H_2O_2$ (20 or 30 volumes) represents, for example, by weight, from 20 to 300%, relative to the weight of the specific dye composition.

The following non-limiting examples illustrate the present invention.

In these examples, the hair dye composition comprises a combination of the hair dye formulation and the shampoo formulation, these formulations to be applied sequentially in the order given.

In these examples: the compound of formula $R'_4$—CHOH—CH_2(OCH_2—CHOH—CH_2)_{3.5}$—OH, wherein $R_4$ is a mixture of $C_9$-$C_{12}$ alkyl radicals is designated compound A;

the compound of formula $R'_5$—$(OC_2H_3(CH_2-OH))_{1-2}$OH wherein $R'_5$ is oleyl is designated compound B;

the compound of formula $R'_5$—$(OC_2H_3(CH_2-OH))_{1-2}$OH wherein $R'_5$ is oleyl is designated compound C;

sodium lauryl ether sulfate oxyethylenated with 2 moles of ethylene oxide (product with 30% active material) is designated compound D;

cationic polymer having units of the formula

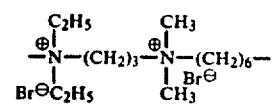

is designated compound E;

the product resulting from the quaternization by dimethyl sulfate of the polyaddition product of N,N'-bis (2,3-epoxy propyl) piperazine and dodecylamine, and described in French Pat. No. 72.42279, is designated compound F;

the polycondensate of piperazine, diglycolamine and epichlorohydrin in molar proportions of 4:1:5, respectively, and described in Example 2 of French Pat. No. 74.27030 is designated compound G;

the product resulting from the quaternization by dimethyl sulfate of the polycondensation product of piperazine, dodecylamine and epichlorohydrin is designated compound H; and the product resulting from the quaternization by dimethyl sulfate of the polycondensation product of piperazine, laurylamine and epichlorohydrin is designated compound J.

A solution of H₂O₂ of "n" volumes is a solution which on decomposition, in accordance with the reaction: $H_2O_2 + \frac{1}{2} O_2$, furnishes "n" liters of oxygen per liter of the initial H₂O₂ solution. Thus a solution of H₂O₂ (20 volumes) contains about 1.8 moles of H₂O₂ (or about 60 g) per liter, and a solution of H₂O₂ (30 volumes) contains about 2.7 moles of H₂O₂ (or about 90 g) per liter.

Example 1—Hair dye formulation in cream form

An oxidation hair dye composition is prepared by admixing:

| | |
|---|---|
| Cetyl stearyl alcohol | 20 g |
| Oleic diethanolamide | 6 g |
| Sodium cetyl stearyl sulfate | 3 g |
| Cationic polymer sold under the mark JR 125 | 1.5 g |
| Ammonia 22° Bé | 12 ml |
| Meta diamino anisol sulfate | 0.048 g |
| Resorcinol | 0.420 g |
| Meta-amino phenol | 0.150 g |
| Nitro paraphenylene diamine | 0.085 g |
| Para toluylene diamine | 0.004 g |
| Ethylene diamine tetraacetic acid | 1.000 g |
| Sodium bisulfite (d = 1.32) | 1.200 g |
| Water, q.s.p. | 100 g |

30 g of this composition are admixed with 45 g of H₂O₂ (20 volumes) to provide hair dye formulation which is in the form of a cream having a smooth consistency which is pleasant to apply and which adheres well to the hair. The resulting cream is applied to the hair and is permitted to remain in contact therewith for 30 minutes. The hair is then rinsed with water and to the thus rinsed hair there are applied 20 g of the following shampoo, in one or two steps.

| Shampoo formulation | |
|---|---|
| Compound A | 2 g |
| Ammonium lauryl sulfate | 12 g |
| Cationic polymer sold under the trade name Gafquat 734 | 1.5 g |
| Water, q.s.p. | 100 g |
| pH = 7.7, clear appearance | |

This shampoo formulation is massaged into the hair so as to develop an abundant foam. The hair is then rinsed with water. On 100% white hair a blond coloration is obtained. The wet hair combs easily and is silky to the touch. The hair is then set and dried. The dry hair is shiny and lively, has body, is silky to the touch, and is easy to comb and style.

Example 2—Hair dye formulation in cream form

An oxidation hair dye composition is prepared by admixing:

| | |
|---|---|
| Cetyl stearyl alcohol | 23 g |
| Oleic diethanolamide | 5 g |
| Sodium cetyl stearyl sulfate | 2.5 g |
| Cationic polymer sold under the tradename JR 400 | 1.0 g |
| Ammonia, 22° Bé | 10 ml |
| Meta-diamino anisol sulfate | 0.048 g |
| Resorcinol | 0.420 g |
| Meta-amino phenol | 0.150 g |
| Nitro paraphenylene diamine | 0.085 g |
| Para toluylene diamine | 0.004 g |
| Ethylenediamine tetraacetic acid | 1.000 g |
| Sodium bisulfite (d = 1.32) | 1.200 g |
| Water, q.s.p. | 100 g |

30 g of this composition are admixed with 45 g of H₂O₂ (20 volumes) to provide a hair dye formulation which is in the form of a cream having a smooth consistency which is pleasant to apply and which adheres well to the hair. The resulting cream is applied to the hair and is permitted to remain in contact therewith for 30 minutes. The hair is then rinsed with water and to the thus rinsed hair there are applied 20 g of the following shampoo, in one or two steps:

| Shampoo formulation: | |
|---|---|
| Compound A | 3 g |
| Triethanolamine lauryl sulfate | 10 g |
| Cationic polymer sold under the trademark Polyquart H | 2 g |
| Water, q.s.p. | 100 g |
| pH = 7, clear appearance | |

This shampoo formulation is massaged into the hair so as to develop an abundant foam. The hair is then rinsed with water. On 100% white hair a blond coloration is obtained. The wet hair combs easily and is silky to the touch. The hair is then set and dried. The dry hair is shiny and lively, has body, is silky to the touch, it combs easily and is easy to style.

Example 3—Hair dye formulation in cream form

An oxidation hair dye composition is prepared by admixing:

| | |
|---|---|
| Cetyl stearyl alcohol | 20 g |
| Oleic diethanolamide | 6 g |
| Sodium cetyl stearyl sulfate | 3 g |
| Cationic polymer sold under the tradename JR 30 M | 0.5 g |
| Ammonia, 22° Bé | 12 ml |
| Meta diamino anisol sulfate | 0.048 g |
| Resorcinol | 0.420 g |
| Meta amino phenol | 0.150 g |
| Nitro paraphenylene diamine | 0.085 g |
| Para toluylene diamine | 0.004 g |
| Ethylene diamine tetraacetic acid | 1.00 g |
| Sodium bisulfite (d = 1.32) | 1.200 g |
| Water, q.s.p. | 100 g |

30 g of this composition are admixed with 45 g of H₂O₂ (20 volumes) to provide a hair dye formulation which is in the form of a cream having a smooth consistency which is pleasant to apply and which adheres well to the hair. The resulting cream is applied to the hair and is permitted to remain in contact therewith for 30 minutes. The hair is then rinsed with water and to the thus rinsed hair there are applied 20 g of the following shampoo, in one or two steps:

| Shampoo formulation: | |
|---|---|
| Compound A | 4 g |
| Triethanolamine lauryl sulfate | 12 g |
| Graft cationic polymer, obtained as described below | 1.5 g |
| Water, q.s.p. | 100 g |
| pH = 7, clear appearance | |

This shampoo formulation is massaged into the hair so as to develop an abundant foam. The hair is then rinsed with water. On 100% white hair a blond coloration is obtained. The wet hair combs easily and is silky to the touch. The hair is then set and dried. The dry hair is shiny and lively, has body, is silky to the touch, and is easy to comb and style.

The graft cationic polymer employed above is obtained by admixing:

| | |
|---|---|
| N-vinylpyrrolidone, freshly distilled | 50.6 g |
| Dimethylaminoethyl methacrylate, quaternized with dimethyl sulfate | 41.25 g |
| Polyethylene glycol (MW-20,000) | |
| Azo bisisobutyronitrile | 0.2 g |
| Ethanol | 20 g |

The resulting mixture is then heated to 65° C. with agitation. When the reaction mixture becomes viscous, an additional 80 g of ethanol previously heated to 65° C. are added. The temperature is then adjusted to 76° C. and agitation is continued for 24 hours. At the end of this period, 200 g of water are introduced and the water-ethanol azeotrope is distilled until all of the ethanol is removed, yielding the above desired polymer having a viscosity of 32 cps, measured in a 2% solution of the polymer in water at a temperature of 34.6° C.

Example 4—Hair dye formulation in cream form

An oxidation hair dye composition is prepared by admixing:

| | |
|---|---|
| Cetyl stearyl alcohol | 22 g |
| Oleic diethanolamide | 5 g |
| Sodium cetyl stearyl sulfate | 2.5 g |
| Ammonia, 22° Bé | 11 ml |
| Meta diamino anisol sulfate | 0.048 g |
| Resorcinol | 0.420 g |
| Meta amino phenol | 0.150 g |
| Nitro paraphenylene diamine | 0.085 g |
| Para toluylene diamine | 0.004 g |
| Ethylene diamine tetraacetic acid | 1.200 g |
| Sodium bisulfite (d = 1.32) | 1.000 g |
| Graft cationic copolymer as described below | 5 g |
| Water, q.s.p. | 100 g |

30 g of this composition are admixed with 45 g of H$_2$O$_2$ (20 volumes) to provide a hair dye formulation which is in the form of a cream having a smooth consistency which is pleasant to apply and which adheres well to the hair. The resulting cream is applied to the hair and is permitted to remain in contact therewith for 30 minutes. The hair is then rinsed with water and to the thus rinsed hair there are applied 20 g of the following shampoo, in one or two steps:

| | |
|---|---|
| Shampoo formulation: | |
| Compound A | 3 g |
| Triethanolamine lauryl sulfate | 8 g |
| Cationic polymer sold under the trade name JR 125 | 0.8 g |
| Sodium ortho phenyl phenate | 0.2 g |
| Ethylene diamine tetraacetic acid | 0.55 g |
| Water, q.s.p. | 100 g |
| pH = 6.8, clear appearance | |

This shampoo formulation is massaged into the hair so as to develop an abundant foam. The hair is then rinsed with water. On 100% white hair a blond coloration is obtained. The wet hair combs easily and is silky to the touch. The hair is then set and dried. The dry hair is shiny and lively, has body, is silky to the touch, and is easy to comb and style.

The graft cationic copolymer used above is obtained by admixing:

| | |
|---|---|
| N-vinylpyrrolidone, freshly distilled | 54.62 g |
| Dimethyl amino ethyl methacrylate | 9.87 g |
| Polyethylene glycol (MW = 20,000) | 8.81 g |
| Azo bisisobutyronitrile | 0.2 g |
| Ethanol, absolute | 20 g |

By operating in essentially the same way outlined in Example 3 for preparing the graft cationic polymer used therein, there is obtained the graft cationic copolymer used herein with a yield of 98% and a viscosity of 11.2 cps, measured in a 2% solution of the polymer in water at a temperature of 34.6° C.

Example 5—Hair dye formulation in cream form

An oxidation hair dye composition is prepared by admixing:

| | |
|---|---|
| Cetyl stearyl alcohol | 23 g |
| Oleic diethanolamine | 6 g |
| Sodium cetyl stearyl sulfate | 3 g |
| Cyclopolymer resulting from the homopolymerization of N,N-dimethyl N,N-diallyl ammonium bromide | 5 g |
| Meta diamino anisol sulfate | 0.048 g |
| Resorcinol | 0.420 g |
| Meta amino phenol | 0.150 g |
| Nitro paraphenylene diamine | 0.085 g |
| Para toluylene diamine | 0.004 g |
| Ethylene diamine tetraacetic acid | 1.100 g |
| Sodium bisulfite (d = 1.32) | 1.200 g |
| Water, q.s.p. | 100 g |

30 g of this composition are admixed with 45 g of H$_2$O$_2$ (20 volumes) to provide a hair dye formulation which is in the form of a cream having a smooth consistency which is pleasant to apply and which adheres well to the hair. The resulting cream is applied to the hair and is permitted to remain in contact therewith for 30 minutes. The hair is then rinsed with water and to the thus rinsed hair there are applied 20 g of the following shampoo, in one or two steps:

| | |
|---|---|
| Shampoo formulation: | |
| Triethanolamine lauryl sulfate | 20 g |
| Cationic polymer sold under the trade name JR 400 | 1.5 g |
| Water, q.s.p. | 100 g |
| pH = 7.8, clear appearance | |

This shampoo formulation is massaged into the hair so as to develop an abundant foam. The hair is then rinsed with water. On 100% white hair, a blond coloration is obtained. The wet hair combs easily and is silky to the touch. The hair is then set and dried. The dry hair is shiny and lively, has body, is silky to the touch and combs and styles easily.

Example 6—Hair dye formulation in cream form

An oxidation hair dye composition is prepared by admixing:

| | |
|---|---|
| Cetyl stearyl alcohol | 22 g |
| Oleic diethanolamine | 5 g |
| Sodium cetyl stearyl sulfate | 2.5 g |
| Copolymer resulting from the copolymerization of 25% N,N-dimethyl, N,N-diallyl ammonium bromide and 75% N-vinylpyrrolidone | 6 g |
| Meta diamino anisol sulfate | 0.048 g |
| Resorcinol | 0.420 g |
| Meta amino phenol | 0.150 g |
| Nitro paraphenylene diamine | 0.085 g |
| Para toluylene diamine | 0.004 g |
| Ethylene diamine tetraacetic acid | 1.200 g |
| Sodium bisulfite (d = 1.32) | 1.200 g |
| Water, q.s.p. | 100 g |

30 g of this composition are admixed with 45 g of $H_2O_2$ (20 volumes) to provide a hair dye formulation which is in the form of a cream having a smooth consistency which is pleasant to apply and which adheres well to the hair. The resulting cream is applied to the hair and is permitted to remain in contact therewith for 30 minutes. The hair is then rinsed with water and to the thus rinsed hair there are applied 20 g of the following shampoo, in one or two steps:

| Shampoo formulation: | |
|---|---|
| Triethanolamine lauryl sulfate | 20 g |
| Cationic polymer sold under the trade name JR 30 M | 0.5 g |
| Water, q.s.p. | 100 g |
| pH 6, cloudy appearance | |

This shampoo formulation is massaged into the hair so as to develop an abundant foam. The hair is then rinsed with water. On 100% white hair a blond coloration is obtained. The wet hair combs easily and is silky to the touch. The hair is then set and dried. The dry hair is shiny and lively, has body, is silky to the touch and is easy to comb and style.

Example 7—Hair dye formulation in gel form

An oxidation hair dye composition in the form of a gellable liquid is prepared by admixing:

| | |
|---|---|
| Compound B | 25 g |
| Compound C | 25 g |
| Cationic polymer E | 4 g |
| Butyl glycol | 8 g |
| Ethyl alcohol (90° titer) | 12 g |
| Ammonia, 22° Bé | 12 ml |
| Para amino phenol | 0.280 g |
| Resorcinol | 0.040 g |
| Meta amino phenol | 0.060 g |
| Nitro para phenylene diamine | 0.020 g |
| Para toluylene diamine | 0.120 g |
| Hydroquinone | 0.170 g |
| Ethylene diamine tetraacetic acid | 3.000 g |
| Sodium bisulfite (d = 1.32) | 0.800 ml |
| Water, q.s.p. | 100 g |

50 g of this gellable liquid are admixed in a bowl with 50 g of $H_2O_2$ (20 volumes) to provide a hair dye formulation which is in the form of a gel.

This gel is then applied to the hair with a brush and is permitted to remain in contact therewith for 30 minutes. The hair is then rinsed with water and to the thus rinsed hair there are applied 20 g of the following shampoo, in one or two steps:

| Shampoo formulation | |
|---|---|
| Compound A | 4 g |
| Triethanolamine lauryl sulfate | 10 g |
| Cationic polymer described in Example 2 of French Patent 74.27030 - Compound G | 2 g |
| Water, q.s.p. | 100 g |
| pH = 7.5, clear appearance | |

This shampoo formulation is massaged into the hair so as to develop an abundant foam. The hair is then rinsed with water. On light chestnut hair a golden blond coloration is obtained. The wet hair combs easily and is silky to the touch. The hair is then set and dried. The dry hair is shiny and lively, has body, is silky to the touch and combs and styles easily.

Example 8—Hair dye formulation in gel form

An oxidation hair dye composition in the form of a gellable liquid is prepared by admixing:

| | |
|---|---|
| Compound B | 25 g |
| Compound C | 25 g |
| Quaternized polymer - Compound K | 5 g |
| Butyl glycol | 6 g |
| Ethyl alcohol (96° titer) | 12 g |
| Ammonia, 22° Bé | 12 ml |
| Para amino phenol | 0.080 g |
| Meta amino anisol sulfate | 0.025 g |
| Resorcinol | 0.300 g |
| Meta amino phenol | 0.060 g |
| Nitro paraphenylene diamine | 0.003 g |
| Para toluylene diamine | 1.050 g |
| Hydroquinone | 0.170 g |
| Ethylenediamine tetraacetic acid | 3.000 g |
| Sodium bisulfite (d = 1.32) | 0.800 g |
| Water, q.s.p. | 100 g |

The quaternized polymer K comprises units of the formula

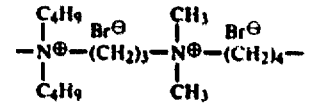

50 g of this gellable liquid are admixed in a bowl with 50 g of $H_2O_2$ (20 volumes) to provide a hair dye formulation which is in the form of a gel. This gel is then applied to the hair with a brush and is permitted to remain in contact therewith for 30 minutes. The hair is then rinsed with water and to the thus rinsed hair there are applied 20 g of the following shampoo in one or two stages.

| Shampoo formulation: | |
|---|---|
| Triethanolamine lauryl sulfate | 20 g |
| Cationic polymer sold under the trade name JR 400 | 1.5 g |
| Water, q.s.p. | 100 g |
| pH = 7.6, clear appearance | |

This shampoo formulation is massaged into the hair so as to develop an abundant foam. The hair is then rinsed with water. On deep chestnut hair a light chestnut coloration is obtained. The wet hair combs easily and is silky to the touch. The hair is then set and dried. The dry hair is shiny and lively, has body, is silky to the touch, and combs and styles easily.

Example 9—Hair lightener formulation in gel form

A hair lightener composition in the form of a gellable liquid is prepared by admixing:

| | |
|---|---|
| Compound B | 5 g |
| Compound D | 20 g |
| Lauric diethanolamide | 12 g |
| Quaternized polymer* | 4 g |
| Butyl glycol | 6 g |
| Propylene glycol | 7 g |
| Ethylene diamine tetraacetic acid | 2 g |
| Ammonia, 22° Bé | 10 ml |
| Water, q.s.p. | 100 g |

*This polymer comprises units of the formula

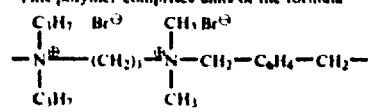

60 g of this gellable liquid are admixed with 60 g of H₂O₂ (20 volumes) in a plastic applicator to provide a hair lightener formulation in the form of a gel. This gel is then applied to the hair and is permitted to remain in contact therewith for 5–10 minutes. The hair is then rinsed with water and to the thus rinsed hair there are applied 20 g of the following shampoo, in one or two steps:

| Shampoo formulation: | |
|---|---|
| Compound A | 4 g |
| Triethanolamine lauryl sulfate | 8 g |
| Cationic polymer described in Example 2 of French Patent No. 74.27030 - Compound G | 2 g |
| Water, q.s.p. | 100 g |
| pH = 7, clear appearance | |

This shampoo formulation is massaged into the hair so as to develop an abundant foam. The hair is then rinsed with water. On chestnut hair, a light chestnut coloration is obtained. The hair combs easily and is silky to the touch. The hair is then set and dried. The dry hair is shiny and lively, has body, is silky to the touch and combs easily.

Example 10—Hair dye formulation in cream form

An oxidation hair dye composition is prepared by admixing:

| | |
|---|---|
| Cetyl stearyl alcohol | 22 g |
| Oleic diethanolamide | 5 g |
| Sodium cetyl stearyl sulfate | 3 g |
| Quaternized polymer* | 5 g |
| Ammonia, 22° Bé | 12 ml |
| Meta diamino anisol sulfate | 0.048 g |
| Resorcinol | 0.420 g |
| Meta amino phenol | 0.150 g |
| Nitro paraphenylene diamine | 0.085 g |
| Para toluylene diamine | 0.004 g |
| Ethylene diamine tetraacetic acid | 1.000 g |
| Sodium bisulfite (d = 1.32) | 1.200 g |
| Water, q.s.p. | 100 g |

*This polymer comprises units of the formula $$-\overset{+}{N}(CH_3)-(CH_2)_n-\overset{+}{N}(CH_3)-(CH_2)_n-$$
   |                          |
   CH₃                        CH₃

30 g of this composition are admixed with 45 g of H₂O₂ (20 volumes) to provide a hair dye formulation which is in the form of a cream having a smooth consistency which is pleasant to apply and which adheres well to the hair. The resulting cream is applied to the hair and is permitted to remain in contact therewith for 30 minutes. The hair is then rinsed with water and to the thus rinsed hair there are applied 20 g of the following shampoo, in one or two steps:

| Shampoo formulation: | |
|---|---|
| Compound A | 2 g |
| Triethanolamine lauryl sulfate | 10 g |
| Cationic polymer described in Example 2 of French Patent No. 74.27030 - Compound G | 1 g |
| Water, q.s.p. | 100 g |
| pH = 7.7, clear appearance | |

This shampoo formulation is massaged into the hair so as to develop an abundant foam. The hair is then rinsed with water. On 100% white hair a blond coloration is obtained. The wet hair combs easily and is silky to the touch. The hair is then set and dried. The dry hair is shiny and lively, has body, is silky to the touch, and combs and styles easily.

Example 11—Hair lightener formulation in gel form

A hair lightener composition in the form of a gellable liquid is prepared by admixing:

| | |
|---|---|
| Compound B | 5 g |
| Compound D | 20 g |
| Lauric diethanolamide | 12 g |
| Compound F | 3 g |
| Butyl glycol | 5 g |
| Propylene glycol | 6.5 g |
| Ethylenediamine tetraacetic acid | 2 g |
| Ammonia, 22° Bé | 10 ml |
| Water, q.s.p. | 100 g |

60 g of this gellable liquid are admixed with 60 g of H₂O₂ (20 volumes) in a plastic applicator to provide a hair lightener formulation in the form of a gel. This gel is then applied to the hair and is permitted to remain in contact therewith for 5–10 minutes. The hair is then rinsed with water and to the thus rinsed hair there are applied 20 g of the following shampoo, in one or two stages:

| Shampoo formulation: | |
|---|---|
| Triethanolamine lauryl sulfate | 20 g |
| Cationic polymer sold under the trade name Polyquart H | 2 g |
| Sodium orthophenyl phenate | 0.2 g |
| Ethylenediamine tetraacetic acid | 0.15 g |
| Water, q.s.p. | 100 g |
| pH = 6.8, clear appearance. | |

This shampoo formulation is massaged into the hair so as to develop an abundant foam. The hair is then rinsed with water. On chestnut hair a light chestnut color is obtained. The wet hair combs easily and is silky to the touch. The hair is then set and dried. The dry hair is shiny and lively, has body, is silky to the touch and combs easily.

Example 12—Hair lightener formulation in gel form

A hair lightener composition in the form of a gellable liquid is prepared by admixing:

| | |
|---|---|
| Compound B | 5 g |
| Compound D | 20 g |
| Lauric diethanolamide | 12 g |
| Compound H | 6 g |
| Butyl glycol | 5 g |
| Propylene glycol | 6.5 g |
| Ethylenediamine tetraacetic acid | 2 g |
| Ammonia, 22° Bé | 10 ml |
| Water, q.s.p. | 100 g |

60 g of this gellable liquid are admixed with 60 g of $H_2O_2$ (20 volumes) in a plastic applicator to provide a hair lightener formulation in the form of a gel. This gel is then applied to the hair and is permitted to remain in contact therewith for 5-10 minutes. The hair is then rinsed with water and to the thus rinsed hair there are applied 20 g of the following shampoo, in one or two steps:

| Shampoo formulation: | |
|---|---|
| Compound A | 3 g |
| Triethanolamine lauryl sulfate | 8 g |
| Cationic polymer sold under the trade name Gafquat 734 | 2 g |
| Water, q.s.p. | 100 g |
| pH = 7.7, clear appearance | |

This shampoo formulation is massaged into the hair so as to develop an abundant foam. The hair is then rinsed with water. On chestnut hair a light chestnut color is obtained. The wet hair combs easily and is silky to the touch. The hair is then set and dried. The dry hair is shiny and lively, has body, is silky to the touch and combs easily.

Example 13—Hair dye formulation in gel form

An oxidation hair dye composition in the form of a gellable liquid is prepared by admixing:

| | |
|---|---|
| Compound B | 25 g |
| Compound C | 25 g |
| Compound H | 6 g |
| Butyl glycol | 3 g |
| Ethyl alcohol 96% | 11 g |
| Ammonia, 22° Bé | 10 ml |
| Para amino phenol | 0.280 g |
| Resorcinol | 0.040 g |
| Meta amino phenol | 0.060 g |
| Nitro paraphenylene diamine | 0.020 g |
| Para toluylene diamine | 0.120 g |
| Ethylene diamine tetraacetic acid | 2.500 g |
| Sodium bisulfite (d = 1.32) | 1.000 g |
| Water, q.s.p. | 100 g |

50 g of this gellable liquid are admixed in a bowl with 50 g of $H_2O_2$ (20 volumes) to provide a hair dye formulation in the form of a gel. This gel is then applied to the hair with a brush and is permitted to remain in contact therewith for 30 minutes. The hair is then rinsed with water and to the thus rinsed hair there are applied 20 g of the following shampoo, in one or two steps:

| Shampoo formulation: | |
|---|---|
| Compound A | 3 g |
| Triethanolamine lauryl sulfate | 12 g |
| Cationic polymer sold under the trade name JR 30 M | 0.3 g |
| Water, q.s.p. | 100 g |
| pH = 6, slightly cloudy appearance | |

This shampoo formulation is massaged into the hair so as to develop an abundant foam. The hair is then rinsed with water. On light chestnut hair a golden blond color is obtained. The wet hair combs easily and is silky to the touch. The hair is then set and dried. The dry hair is shiny and lively, has body, is silky to the touch, and combs and styles easily.

Example 14—Hair dye formulation in cream form

An oxidation hair dye composition is prepared by admixing:

| | |
|---|---|
| Cetyl stearyl alcohol | 23 g |
| Oleic diethanolamide | 6 g |
| Sodium cetyl stearyl sulfate | 3 g |
| Compound F | 4 g |
| Ammonia, 22° Bé | 11 ml |
| Meta diamino anisol sulfate | 0.048 g |
| Resorcinol | 0.420 g |
| Meta amino phenol | 0.150 g |
| Nitro paraphenylene diamine | 0.085 g |
| Para toluylene diamine | 0.004 g |
| Ethylene diamine tetraacetic acid | 1.000 g |
| Sodium bisulfite (d = 1.32) | 2 g |
| Water, q.s.p. | 100 g |

30 g of this composition are admixed with 45 g of $H_2O_2$ (20 volumes) to provide a hair dye formulation which is in the form of a cream having a smooth consistency which is pleasant to apply and which adheres well to the hair. The resulting cream is applied to the hair and is permitted to remain in contact therewith for 30 minutes. The hair is then rinsed with water and to the thus rinsed hair there are applied 20 g of the following shampoo in one or two steps:

| Shampoo formulation: | |
|---|---|
| Triethanolamine lauryl sulfate | 20 g |
| Cationic polymer sold under the trade name JR 400 | 1.5 g |
| Water, q.s.p. | 100 g |
| pH = 7.6, clear appearance | |

This shampoo formulation is massaged into the hair so as to develop an abundant foam. The hair is then rinsed with water. On 100% white hair a blond coloration is obtained. The wet hair combs easily and is silky to the touch. The hair is then set and dried. The dry hair is shiny and lively, has body, is silky to the touch and combs and styles easily.

Example 15—Hair dye formulation in cream form

An oxidation hair dye composition is prepared by admixing:

| | |
|---|---|
| Cetyl stearyl alcohol | 22 g |

| -continued | |
|---|---|
| Oleic diethanolamide | 5 g |
| Sodium cetyl stearyl sulfate | 2.5 g |
| Compound H | 5 g |
| Ammonia, 22° Bé | 12 ml |
| Meta diamino anisol sulfate | 0.048 g |
| Resorcinol | 0.420 g |
| Meta amino phenol | 0.150 g |
| Nitro paraphenylene diamine | 0.085 g |
| Para toluylene diamine | 0.004 g |
| Ethylene diamine tetraacetic acid | 1.200 g |
| Sodium bisulfite (d = 1.32) | 1.200 g |
| Water, q.s.p. | 100 g |

30 g of this composition are admixed with 45 g of $H_2O_2$ (20 volumes) to provide a hair dye formulation which is in the form of a cream having a smooth consistency and which is pleasant to apply and which adheres well to the hair. The resulting cream is applied to the hair and is permitted to remain in contact therewith for 30 minutes. The hair is then rinsed with water and to the thus rinsed hair there are applied 20 g of the following shampoo, in one or two steps:

| Shampoo formulation: | | |
|---|---|---|
| Triethanolamine lauryl sulfate | 20 | g |
| Quaternized polymer* | 0.5 | g |
| Water, q.s.p. | 100 | g |
| pH = 6.9, clear appearance | | |

*This polymer comprises units of the formula:

$$\overset{\oplus}{N}\text{---}(CH_2)_6\text{---}\overset{\oplus}{N}\text{---}CH_2\text{---}CHOH\text{---}CH_2\text{---}$$
with $CH_3$, $CH_3$ substituents and $Cl^\ominus$ counterions.

This shampoo formulation is massaged into the hair so as to develop an abundant foam. The hair is then rinsed with water. On 100% white hair a blond coloration is obtained. The wet hair combs easily and is silky to the touch. The hair is then set and dried. The dry hair is shiny and lively, has body, is silky to the touch, and combs and styles easily.

EXAMPLE 16—Hair dye formulation in cream form

An oxidation hair dye composition is prepared by admixing:

| | |
|---|---|
| Cetyl stearyl alcohol | 23 g |
| Oleic diethanolamide | 5 g |
| Sodium cetyl stearyl sulfate | 2.5 g |
| Compound J | 4 g |
| Ammonia, 22° Bé | 12 ml |
| Meta diamino anisol sulfate | 0.048 g |
| Resorcinol | 0.420 g |
| Meta amino phenol | 0.150 g |
| Nitro paraphenylene diamine | 0.085 g |
| Para toluylene diamine | 0.004 g |
| Ethylene diamine tetraacetic acid | 1.000 g |
| Sodium bisulfite (d = 1.32) | 1.200 g |
| Water, q.s.p. | 100 g |

30 g of this composition are admixed with 45 g of $H_2O_2$ (20 volumes) to provide a hair dye formulation which is in the form of a cream having a smooth consistency and which is pleasant to apply and which adheres well to the hair. The resulting cream is applied to the hair and is permitted to remain in contact therewith for 30 minutes. The hair is then rinsed with water and to the thus rinsed hair there are applied 20 g of the following shampoo, in one or two steps:

| Shampoo formulation: | | |
|---|---|---|
| Compound A | 4 | g |
| Ammonium lauryl sulfate | 10 | g |
| Quaternized polymer* | 0.5 | g |
| Water, q.s.p. | 100 | g |
| pH = 6.2, clear appearance | | |

*This polymer comprises units of the formula:

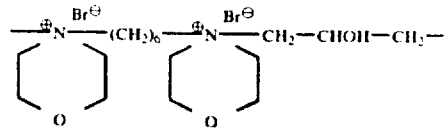

This shampoo formulation is massaged into the hair so as to develop an abundant foam. The hair is then rinsed with water. On 100% white hair a blond color is obtained. The wet hair combs easily and is silky to the touch. The hair is then set and dried. The dry hair is shiny and lively, has body, is silky to the touch, and combs and styles easily.

EXAMPLE 17—Hair dye formulation in cream form

An oxidation hair dye composition is prepared by admixing:

| | |
|---|---|
| Cetyl stearyl alcohol | 20 g |
| Oleic diethanolamide | 4 g |
| Sodium cetyl stearyl sulfate | 3 g |
| Cationic polymer | 5 g |
| Ammonia, 22° Bé (11N) | 10 ml |
| Meta diamino anisol sulfate | 0.048 g |
| Resorcinol | 0.420 g |
| Meta-amino phenol | 0.150 g |
| Nitro paraphenylene diamine | 0.085 g |
| Para toluylene diamine | 0.004 g |
| Trilon B, ethylene diamine tetraacetic acid | 1 g |
| Sodium bisulfite (d = 1.32) | 1.200 g |
| Water, q.s.p. | 100 g |

30 g of this composition are admixed with 45 g of $H_2O_2$ (20 volumes) to provide a hair dye formulation in the form of a cream having a smooth consistency and which is pleasant to apply and which adheres well to the hair. The resulting cream is applied to the hair and is permitted to remain in contact therewith for 30 minutes. The hair is then rinsed with water and to the thus rinsed hair there are applied 20 g of the following anionic shampoo:

| Shampoo formulation: | |
|---|---|
| Triethanolamine lauryl sulfate | 10 g |
| Cationic polymer | 1 g |
| Triethanolamine, q.s.p. pH = 8 | |
| Water, q.s.p. | 100 g |

This shampoo formulation is massaged into the hair so as to develop an abundant foam. The hair is then rinsed with water. On 100% white hair a blond color is obtained. The hair, wet or dry, combs easily, has a shiny appearance and is pleasant and silky to the touch.

The cationic polymer employed in the oxidation hair dye composition comprises units of formula X' wherein $R_1=R_2=R_3=R_4=R_5=CH_3$; $A=(CH_2)_{10}$; $B=(CH_2)_6$; and $X=Br$.

The cationic polymer used in the shampoo formulation comprises units of formula IX wherein $R_1=R_2=R_3=R_4=R_5=CH_3$; $A=(CH_2)_2$;

$B = B_1 = (CH_2)_4$; $X = Y—Br$. This polymer is prepared using 1.4 moles of dihalide per mole of triamine.

EXAMPLE 18—Hair dye formulation in cream form

An oxidation hair dye composition is prepared by admixing:

| | |
|---|---|
| Cetyl stearyl alcohol | 22 g |
| Oleic diethanolamide | 5 g |
| Sodium cetyl stearyl sulfate | 4 g |
| Cationic polymer | 3 g |
| Ammonia, 22° Bé | 12 ml |
| Meta diamino anisol sulfate | 0.048 g |
| Resorcinol | 0.420 g |
| Meta amino phenol | 0.150 g |
| Nitro paraphenylene diamine | 0.085 g |
| Para toluylene diamine | 0.004 g |
| Trilon B | 1.000 g |
| Sodium bisulfite (d = 1.32) | 1.200 g |
| Water, q.s.p. | 100.000 g |

30 g of this composition are admixed with 45 g of $H_2O_2$ (20 volumes) to provide a hair dye formulation in the form of a cream having a smooth consistency which is pleasant to apply and which adheres well to the hair. The resulting cream is then applied to the hair and is permitted to remain in contact therewith for 30 minutes. The hair is then rinsed with water and to the thus rinsed hair there are applied 20 g of the following anionic shampoo:

| Shampoo composition: | |
|---|---|
| Triethanolamine lauryl sulfate | 10 g |
| Cationic polymer | 1.5 g |
| Triethanolamine, q.s. pH = 8 | |
| Water, q.s.p. | 100 g |

This shampoo formulation is massaged into the hair so as to develop an abundant foam. The hair is then rinsed with water. On 100% white hair a blond color is obtained. The combing of the hair, wet or dry is easy. The hair is dried and the dry hair has a shiny appearance, and is pleasant and silky to the touch.

The cationic polymer used in the oxidation hair dye composition is a polymer of formula IX wherein $B_1 = B = (CH_2)_4$, $R_1 = R_2 = R_3 = R_4 = R_5 = CH_3$, $A = (CH_2)_2$ and $X = Y = Br$. It is prepared in the following manner:

There is heated at reflux for 100 hours a mixture of 17.30 g (0.1 mole) of pentamethyl diethylene triamine and 32.4 g (0.15 mole) of 1,4-dibromo butane in 190 cc of methanol. The reaction mixture is then concentrated under reduced pressure, and the residue is taken up in ethyl ether. The resulting precipitate is filtered and dried under a vacuum in the presence of phosphoric anhydride. The cationic polymer obtained contains 40.5% $Br^{\ominus}$ and is soluble in water.

The cationic polymer used in the shampoo formulation is a polymer of formula X' wherein $R_1 = R_2 = R_3 = R_4 = R_5 = CH_3$; $A = B = (CH_2)_6$; and $X = Br$. This cationic polymer of formula X' can be replaced, in this shampoo formulation, by 1.3 g of the cationic polymer of formula X" wherein $R_1 = R_2 = R_3 = R_4 = R_6 = CH_3$; $R_5 = benzyl$, $A = (CH_2)_2$; $B = (CH_2)_6$, $X^{\ominus} = BR^{\ominus}$ and $Y^{\ominus} CH_3SO_4^{\ominus}$. To obtain this polymer there is employed in the quaternization reaction 0.5 mole of dimethyl sulfate (compound $R_6Y$) per mole of the initial triamine reactant.

What is claimed is:

1. A composition for dyeing hair comprising a combination of two formulations, one to be applied to the hair immediately after the other, the first to be applied formulation being an effective amount of a hair dye formulation comprising a mixture of an oxidation hair dye composition containing at least one hair dye or dye precursor and a hair dye carrier, an oxidizing agent and at least one cationic polymer and the last to be applied formulation being an effective amount of a shampoo formulation comprising an anionic detergent, said hair dye formulation being packaged into two parts, one part comprising said hair dye carrier and said hair dye or dye precursor, and said other part comprising said cationic polymer alone or in solution in a solvent, said two parts being admixed at the time of use.

* * * * *